United States Patent
Hartman et al.

(10) Patent No.: US 6,235,761 B1
(45) Date of Patent: May 22, 2001

(54) COMPOUND, COMPOSITION AND METHOD FOR TREATING CANCER

(76) Inventors: Neil Hartman, 1708 Farragut Ave., Rockville, MD (US) 20851; Robert F. Struck, 3533 Laurel View La., Birmingham, AL (US) 35216; Seamus O'Reilly, 4 Blackthorne Drive, Grantstown Village, Waterford (IE); John M. Strong, 13103 Bluhill Rd., Wheaton, MD (US) 20906; Eric K. Rowinsky, 17110 Spotted Eagle, San Antonio, TX (US) 78248; Jerry M. Collins, 1512 Auburn Ave., Rockville, MD (US) 20850

( * ) Notice: Subject to any disclaimer, the term of this patent is extended or adjusted under 35 U.S.C. 154(b) by 0 days.

(21) Appl. No.: 09/194,490
(22) PCT Filed: Jun. 3, 1997
(86) PCT No.: PCT/US97/09428
 § 371 Date: Feb. 22, 1999
 § 102(e) Date: Feb. 22, 1999
(87) PCT Pub. No.: WO97/46531
 PCT Pub. Date: Dec. 11, 1997

Related U.S. Application Data
(60) Provisional application No. 60/019,086, filed on Jun. 3, 1996.

(51) Int. Cl.[7] ............... C07D 213/69; C07D 213/70; A61K 31/44
(52) U.S. Cl. .......................... 514/348; 546/296
(58) Field of Search ............... 546/296; 514/348

(56) References Cited

U.S. PATENT DOCUMENTS
4,717,726 * 1/1988 Tobol ................. 514/348

OTHER PUBLICATIONS
Berlin et al., "Phase I and Pharmacokinetic Trial of Penclomedine", Proceedings of the American Association for Cancer Research Annual Meetings, 36, 389 (Mar. 1995).

Hartman et al., "Murine and Human in Vivo Penclomedine Metabolism", *Clinical Cancer Research*, 2 6, 953–962 (Jun. 1996).

Hartman et al., "The in Vivo Metabolism of Penclomedine (NSC 338720)", Abstract and poster presented at the American Association for Cancer Research Annual Meeting, Canada (Mar. 1995).

O'Reilly et al., "Tissue and Tumor Distribution of 14C–Penclomedine in Rats", *Clinical Cancer Research*, 2 3, 541–548 (Mar. 1996).

O'Reilly et al., "Tissue and Tumor Distribution of 14C–Penclomedine and it's Metabolites in Rats With and Without Brain Tumors", Proceedings of the American Association for Cancer Research, 36, 362 (Mar. 1995).

(List continued on next page.)

*Primary Examiner*—Alan L. Rotman
(74) *Attorney, Agent, or Firm*—Leydig, Voit & Mayer, Ltd.

(57) ABSTRACT

Substantially pure 3,5-dichloro-2-nethoxy-4-hydroxy-6-(trichloromethyl)pyridine or 4-demethylpenclomedine (formula I), acid addition salts thereof, pharmaceutical compositions containing the aforesaid compound, and a method of using the compound in the treatment of cancer in a mammal are disclosed.

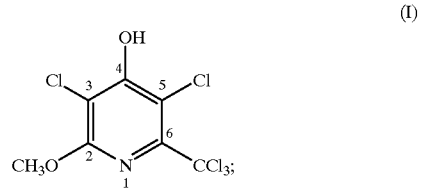

17 Claims, 2 Drawing Sheets

Plowman et al., "Preclinical Antitumor Activity of an α–Picoline Derivative, Penclomedine (NSC 338720), on Human and Murine Tumors", *Cancer Research* 49 1909–1915 (1989).

Waud et al., "4–Demethylpenclomedine, an Antitumor–Active, Potentially Nonneurotoxic Metabolite of Penclomedine", *Cancer Research,* 57 5, 815–817 (Mar. 1997).

* cited by examiner

COMPOUND, COMPOSITION AND METHOD FOR TREATING CANCER

CROSS-REFERENCE TO A RELATED APPLICATION

This application is a 371 of PCT/US97/09428 filed Jun. 3, 1997 which the claims the benefit of Provisional application Ser. No. 60/019,086, filed Jun. 3, 1996.

TECHNICAL FIELD OF THE INVENTION

This invention relates to 4-demethylpenclomedine, a pharmaceutical composition comprising 4-demethylpenclomedine, and a method of using the compound in the treatment of cancer in a mammal.

BACKGROUND OF THE INVENTION

It has been estimated that approximately one out of every three Americans will develop cancer at some point during life. Currently, in spite of intensive research and some major advances in treatment, cancer claims the life of nearly one out of every four Americans.

It is indisputable, therefore, that a cure for the various types of cancer is highly needed. Several cancer chemotherapeutic drugs are known, for example, carmustine, doxorubicin, methotrexate, TAXOL®, nitrogen mustard, procarbazine, and vinblastine, to name only a few.

Many of the chemotherapeutic drugs also produce undesirable side effects in the patient. For example, U.S. Pat. No. 4,717,726 reportedly discloses a compound suitable for inhibiting the growth of certain types of malignant neoplasms in mammals. See also Plowman et al., *Cancer Res.*, 12, 1909–1915 (1989). The disclosed compound, 3,5-dichloro-2,4-dimethoxy-6-(trichloromethyl)pyridine, also known as penclomedine, is not satisfactory as a chemotherapeutic, however, because it is known to produce certain undesirable side effects especially in the central nervous system.

Neurological and hematological toxicities of penclomedine have been reported in preclinical and early clinical studies. Dose related neurotoxicity, consisting of muscle tremors, incoordination, convulsions and reduced activity, has been observed in rats. Neurotoxicity appears to be related to peak plasma drug concentrations, as it developed during or immediately after infusion and could be ameliorated by decreasing the rate of drug administration. In dogs, severe emesis and seizures have been associated with plasma penclomedine levels above 30 μM. Neurotoxicity, consisting of dysmetria, ataxia, and vertigo, was also the principal dose limiting toxicity of penclomedine administered as a one hour infusion for 5 consecutive days in patients with advanced solid tumors. The presence of these toxicities, at much lower peak plasma concentrations compared to those reported in preclinical studies, may preclude the administration of higher doses of penclomedine and the achievement of concentrations associated with optimal antitumor activity. Berlin et al., *Proc. Amer. Assoc. Cancer Res.*, 36, 238 (1995); O'Reilly et al., *Proc. Amer. Soc. Clin. Oncol.*, 14, 471 (1995).

Some relevant background art can be found in O'Reilly et al., *Clinical Cancer Research*, 2, 541–548 (March 1996). This reference describes a study to assess the distribution of $^{14}$C-penclomedine in the tissues and tumors of tumor-bearing rats. The study found that the predominant radioactive species in the brain was $^{14}$C-penclomedine which may explain the observed neurotoxicity of the drug.

Thus, while penclomedine has been tried as an antitumor agent, there remains a need for improved drugs that are effective in combating cancer, but at the same time produce relatively reduced side effects in the patient. An object of the invention, therefore, is to address the above need.

SUMMARY OF THE INVENTION

The present invention provides a substantially pure 3,5-dichloro-2-methoxy-4-hydroxy-6-(trichloromethyl)-pyridine or 4-demethylpenclomedine of the formula (I),

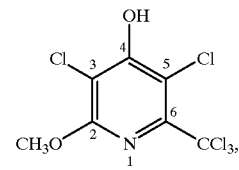

pharmaceutically acceptable salts thereof, pharmaceutical compositions containing the aforesaid compound, and methods of using the compound in the treatment of cancer in a mammal. The compound of the present invention can be in an isolated, purified, or synthetic form.

While the invention is described and disclosed below in connection with certain preferred embodiments and procedures, it is not intended to limit the invention to those specific embodiments. Rather it is intended to cover all such alternative embodiments and modifications as fall within the spirit and scope of the claim.

DETAILED DESCRIPTION OF THE PREFERRED EMBODIMENTS

Figure 1:
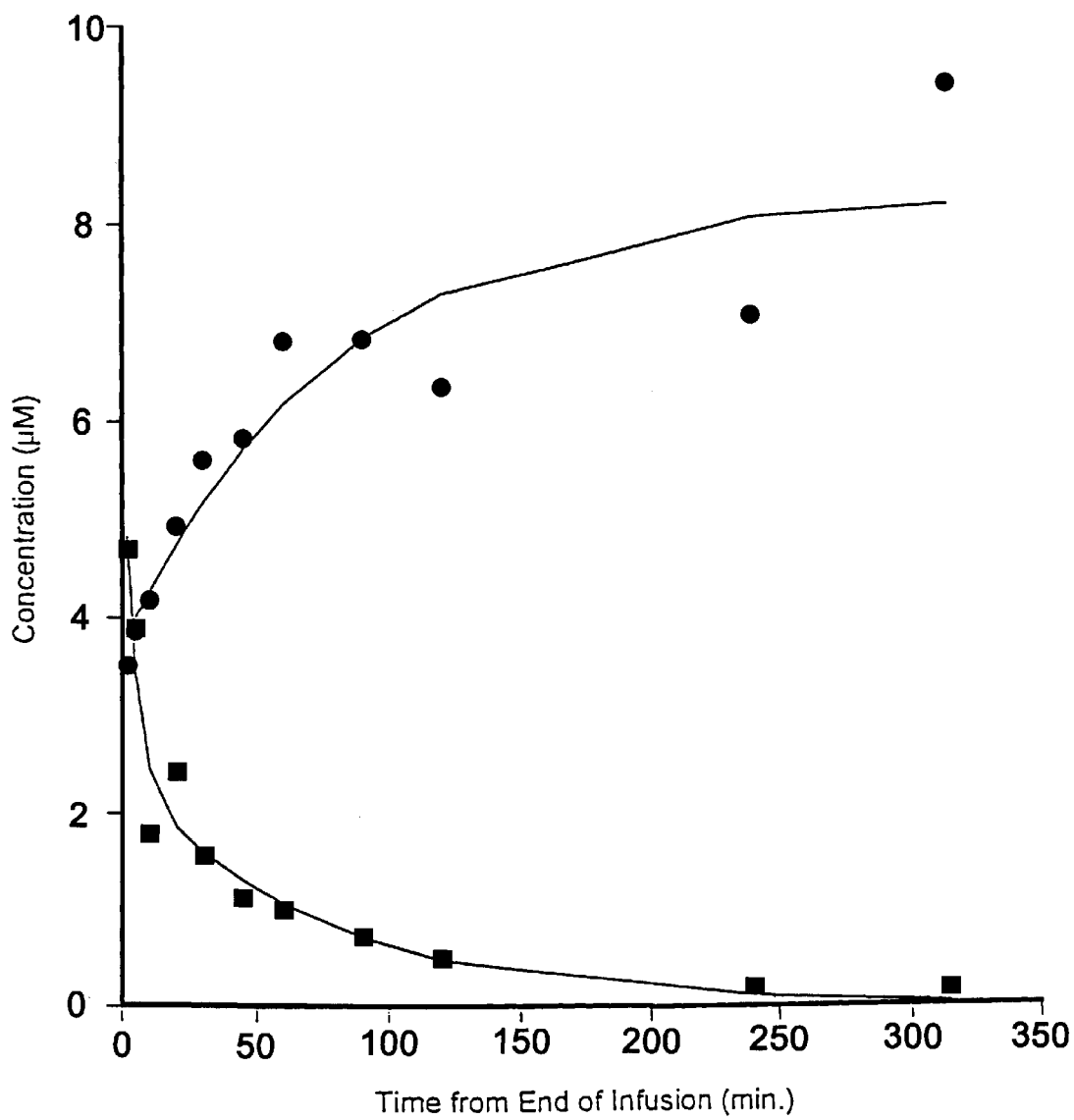
FIG. 1 depicts levels of penclomedine and the demethylpenclomedine metabolite in human plasma, as determined by HPLC chromatographic analysis with uv detection. These results are for a single patient and are typical. ●=Demethylpenclomedine; ■=Penclomedine. The displayed curves were fit using a biexponential decay for penclomedine ($\alpha$=3.88 hr$^{-1}$, $\beta$=0.456 hr$^{-1}$) and an exponential rise to a constant value for demethyl-penclomedine. The Figure shows that penclomedine is rapidly cleared from plasma whereas the metabolite, 4-demethylpenclomedine, continues to increase with time.

The present invention provides a substantially pure 3,5-dichloro-2-methoxy-4-hydroxy-6-(trichloromethyl)-pyridine or 4-demethylpenclomedine of the formula (I),

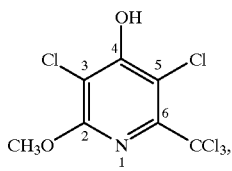

pharmaceutically acceptable salts thereof, pharmaceutical compositions containing the aforesaid compound, and methods of using the compound in the treatment of cancer in a mammal. The compound of the present invention can be in an isolated, purified, or synthetic form.

In accordance with one aspect of the present invention, it has been found that a metabolite of penclomedine, 4-demethylpenclomedine, is surprisingly and advantageously useful in the treatment of mammalian cancer, especially human cancer, owing to its potentially reduced incidence of neurotoxicity, particularly as compared to its parent compound penclomedine.

It has been observed that 4-demethylpenclomedine was present in clinical samples and continued to be present in the plasma for longer than 24 hours. Even after repeated administration of penclomedine, the plasma levels of 4-demethylpenclomedine was observed to reach greater than ten times the peak plasma level of penclomedine, and thus the demethylpenclomedine produced drug exposures of several hundred times that of the parent compound. In fact, the levels of this metabolite increased as toxicity due to penclomedine resolved; and on repeated administration of penclomedine neurotoxicity did not increase while levels of this metabolite increased to several times the plasma levels of the parent drug. These observations suggest that the parent drug rather than 4-demethylpenclomedine mediates neurologic effects.

Penclomedine also is believed to act as a prodrug and thus it needs to be metabolized for it to be active against cancer. Liver function and metabolic rates can affect efficacy. In addition, foods or other drugs present in the body of the mammal during the administration of penclomedine may induce food-penclomedine or drug-penclomedine interactions, which may affect the efficacy of penclomedine.

In keeping with the present invention, 4-demethylpenclomedine can be used alone or in appropriate association, and also may be used in combination with pharmaceutically acceptable carriers and other pharmaceutically active compounds such as other cancer treatment drugs. 4-Demethylpenclomedine also may be used as its acid addition salts. The active agent may be present in the pharmaceutical composition in any suitable quantity.

Examples of pharmaceutically acceptable acid addition salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable carriers described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

4-Demethylpenclomedine alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkylimidazoline quaternary ammonium salts, and (e) mixtures thereof.

The parenteral formulations will typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agents, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., 238–250 (1982), and *ASHP Handbook on Injectable Drugs*, Toissel, 4th ed., 622–630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an animal are available, and, although more than one route can be used to administer a particular compound, a particular route can provide a more immediate and more effective reaction than another route.

The present invention further provides a method of treating cancer in a mammal, especially humans. The method comprises administering an effective treatment amount of 4-demethylpenclomedine to the mammal.

As regards these applications, the present inventive method includes the administration to an animal, particularly a mammal, and more particularly a human, of a therapeutically effective amount of the compound effective in the inhibition of neoplasia and tumor growth.

The compound and compositions of the present invention can be administered to treat a number of cancers, including leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms'Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The method of the present invention is particularly applicable in the treatment of brain, colon, renal, and mammary tumors, and preferably colon, renal and mammary tumors. The method of the present invention can be practiced on mammals, particularly humans.

The dose administered to an animal, particularly a human, in the context of the present invention should be sufficient to effect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to effect the desired response. The preferred dosage is the amount which results in maximum inhibition of cancer, without unmanageable side effects.

The total amount of the compound of the present invention administered in a typical treatment is preferably between about 60 mg/kg and about 2000 mg/kg of body weight for mice, and between about 5 mg/kg and about 100 mg/kg of body weight and more preferably between 5 mg/kg and about 20 mg/kg of body weight for humans. This total amount is typically, but not necessarily, administered as a series of smaller doses over a period of from about one day to about 24 months, and preferably over a period of 28 days to about 12 months.

The size of the dose also will be determined by the route, timing and frequency of administration as well as the existence, nature, and extent of any adverse side-effects that might accompany the administration of the compound and the desired physiological effect. It will be appreciated by one of skill in the art that various conditions or disease states, in particular chronic conditions or disease states, may require prolonged treatment involving multiple administrations.

The method of the present invention comprises further administering a chemotherapeutic agent other than 3,5-dichloro-2-methoxy-4-hydroxy-6-(trichloromethyl)pyridine. Any suitable chemotherapeutic agent can be employed for this purpose. The chemotherapeutic agent is preferably selected from the group consisting of alkylating agents, antimetabolites, natural products, hormonal agents, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside, fluorouracil, gemcitabine, hydroxyurea, mercaptopurine, methotrexate, thioguanine, floxuridine, fludarabine, cadribine, and L-asparaginase.

Examples of chemotherapeutic agents that are natural products include actinomycin D, bleomycin, camptothecins, daunomycin, doxorubicin, etoposide, mitomycin C, TAXOL (paclitaxel), taxotere, teniposide, vincristine, vinorelbine, mithramycin, idarubicin, MITHRACIN™ (plicamycin), and deoxycoformycin.

An example of hormonal chemotherapeutic agent includes tamoxifen. Examples of the aforesaid miscellaneous chemotherapeutic agents include mitotane, mitoxantrone, vinblastine, and levamisole.

Demethylpenclomedine can be prepared by any method known to those of ordinary skill in the art. For example, it can be prepared by heating penclomedine in anhydrous dimethylsulfoxide. Thus, a 200 mM solution of penclomedine in anhydrous dimethylsulfoxide (DMSO) can be held at a temperature of about 120–180° C. for about 30 minutes to about 2 hours, and preferably at a temperature of about 150° C. for about 90 minutes. The principal products are demethylpenclomedine and demethylpenclomic acid. Demethylpenclomedine can be separated and purified by methods known to those of ordinary skill in the art. For example, DMSO can be removed by evaporation under vacuum, the residue dissolved in chloroform, and demethylpenclomic acid extracted into water. Demethylpenclomedine can be further purified by precipitation from methanol/water. Penclomedine can be prepared by any method known to those of ordinary skill in the art, including that set forth in U.S. Pat. No. 4,717,726. Thus, penclomedine can be prepared by combining 2,3,4,5-tetrachloro-6-(trichloromethyl)pyridine with about two or more molar equivalents of an alkali metal methoxide in an organic solvent under conditions conducive to the formation of 3,5-dichloro-2,4-dimethoxy-6-(trichloromethyl)pyridine as a reaction product, and thereafter, recovering the product.

The following examples further illustrate the present invention but, of course, should not be construed as in any way limiting its scope.

EXAMPLE 1

This Example illustrates a method of synthesis of 4-demethylpenclomedine.

Penclomedine (6.38 g, prepared from 2-trichloromethyl-3,4,5,6-tetrachloropyridine) in 20 ml of DMSO was heated with stirring to 150° C. in 15 min. and maintained at 150–160° C. with stirring for 45 min. The reaction solution was frozen and lyophilized, and the residue was stirred with 50 ml of ether. The ether solution was decanted from an insoluble syrup, and the ether solution mixed with 100 ml of hexane. The mixture was allowed to stand at room temperature until the supernate was clear. The supernate was then decanted from the insoluble oil and dried over anhydrous sodium sulfate. The dried solution was decanted from the sodium sulfate and concentrated in vacuo with stirring to 20 ml, during which time a crystalline solid precipitated. The precipitate was collected by filtration and dried in vacuo: yield, 3.8 g (62%). FABMS analysis: $(M+1)^+ 310$ (5Cl); TLC homogeneous on silica gel in methylene chloride: methanol (9:1); TLC after reaction with excess diazomethane indicated essentially complete conversion to penclomedine with a trace of immobile impurity in hexane:methylene chloride (1:1).

$^1$HNMR(CDCl$_3$): δ4.09 ppm (Ar—O—$\underline{CH_3}$ at 2-position).

EXAMPLE 2

This Example illustrates the efficacy of penclomedine and 4-demethylpenclomedine in the treatment of cancer. MX-1 mammary tumor xenograft was subcutaneously implanted into mice, and the mice were exposed to the compounds. The testing of the mice was performed following a published procedure. See, e.g., Plowman et al., supra; Geran et al., *Cancer Chemother. Rep.*, Part 2, 1–55 (1972); Developmental Therapeutics Program, Division of Cancer Treatment, NCI, in In Vivo Models 1976–1982, NIH Publication No. 84-2635, Washington D.C., U.S. Govt. Printing Office (1984).

The results obtained are set forth in Table 1 and confirm that the compound of the present invention is effective in treating cancer. Although administration of penclomedine resulted in a slightly higher survival rate, penclomedine and 4-demethylpenclomedine yielded identical tumor growth delay. Furthermore, penclomedine is neurotoxic to mammals, especially to humans, whereas 4-demethylpenclomedine is not.

TABLE 1

Response of Subcutaneously-Implanted MX-1 Mammary Tumor Xenograft to
Treatment With Penclomedine and 4-Demethylpenclomedine (DM-PEN)

| Treatment[1] | | | | Number of Non-Specific Deaths[2]/ | Tumor Regression[3] | | Duration[4] Med/Range | Tumor Free Survival/ | Days[6] to | Days[7] Delay |
| --- | --- | --- | --- | --- | --- | --- | --- | --- | --- | --- |
| Agent | Dose mg/kg | Route | Schedule | Total | Partial | Complete | (Days) | Total[5] | 2 Doublings | (T-C) |
| Control | 0 | IP | Q 1 n × 5 Day 12 | | | | | 0/10 | 8.0 | |
| Penclomedine | 135 | IP | Q 1 n × 5 Day 12 | 0/5 | 0 | 5 | UE | 5/5 | >49.0 | >41.0 |
| Penclomedine | 90 | IP | Q 1 n × 5 Day 12 | 0/5 | 0 | 5 | UE | 5/5 | >49.0 | >41.0 |
| Penclomedine | 60 | IP | Q 1 n × 5 Day 12 | 0/5 | 0 | 5 | UE | 4/5 | >49.0 | >41.0 |
| DM-PEN | 135 | IP | Q 1 n × 5 Day 12 | 1/5 | 0 | 4 | 35.7 (35–36) | 3/5 | >49.0 | >41.0 |
| DM-PEN | 90 | IP | Q 1 n × 5 Day 12 | 0/5 | 0 | 5 | 32.5 (30–35) | 3/5 | >49.0 | >41.0 |
| DM-PEN | 60 | IP | Q 1 n × 5 Day 12 | 0/5 | 0 | 2 | UE | 2/5 | 23.4 | 15.4 |

[1]Treatment started on Day 12 following tumor implant.
[2]Nonspecific deaths: A treated, tumored animal was presumed to be a nonspecific death if its day of death was significantly less ($p < 0.05$) than the corresponding day of death in the untreated control group and its tumor was less than 400 mg, or if it died with a tumor of 400 mg or less prior to 45 days after the last day of treatment, or with a regressing tumor prior to 15 days after the last day of treatment, or if the treated animal was uniquely specified as a nonspecific death on data input.
[3]Tumor regression was scored (excluding nonspecific deaths), according to the smallest tumor size attained after the beginning of treatment relative to the size at first treatment:
Partial: <50 percent of its size at 1st treatment, but not complete.
Complete: tumor becomes unpalpable.
[4]Duration of regression: the interval during which a tumor classified as a partial or complete regressor was below 50 percent of its size at first treatment.
[5]Evaluation size: this value is the tumor mass selected at one or two mass doublings beginning with the initial tumor size at the start of treatment.
[6]Time required for tumor mass doubling: the time required for a tumor to double in mass is calculated based on the initial tumor weight at the beginning of the treatment period. When the initial tumor weight has been selected, tumor weights are then examined, beginning with the last recorded value, until a doubling is calculated. Examination from the last recorded value is to insure that the doubling time is calculated during the final phase of tumor growth and not prior to a tumor regression. Values between measurements are calculated by exponential extrapolation, and a value may be estimated after the final measured weight provided the extrapolated value occurs prior to the animal's death.
[7]T-C (days): the difference in the median of times postimplant for tumors of the treated groups to attain as evaluation size compared to the median of the control group. The t-c value is measured excluding nonspecific deaths, tumor-free survivors, and any other animal whose tumor failed to attain the evaluation size.

EXAMPLE 3

This Example further illustrates the efficacy of penclomedine and 4-demethylpenclomedine in the treatment of cancer. The compounds were tested in vivo on mice by the procedure set forth in Example 2. The results obtained are set forth in Table 2 and confirm that 4-demethylpenclomedine is active against cancer, particularly mammary, colon, and renal cancer. As can be seen from Table 2, the difference in the median of times poststaging for tumors to double in mass of the treated (T) vs. control (C), i.e., T-C, confirms that the compound of the present invention is active against MX-1, colon, and renal tumors. As discussed earlier, although penclomedine produced a slightly higher survival rate than 4-demethylpenclomedine, the two compounds produced nearly identical T-C. These results further confirm the efficacy of 4-demethylpenclomedine in reducing tumor growth.

TABLE 2

Antitumor Activity of 4-Demethylpenclomedine and Penclomedine

| Tumor[a] | Optimal IP Dosage ($\leq LD_{10}$) (mg/kg/dose) | Schedule (days) | Median % ILS[c] (dying mice only) | T-C[b] (days) | Tumor-Free Survival/Total |
| --- | --- | --- | --- | --- | --- |
| 4-Demethylpenclomedine | | | | | |
| sc MX-1 | 90 | 12–16 | — | >41.0 | 3/5 |
| ic MX-1 | 90 | 1–5 | +60 | — | 0/5 |
| ic MX1-1 | 135[d,e] | 1–5 | +66 | — | 1/5 |
| sc MX-1 | 135[d,e] | 13–17 | — | 36.7 | 2/5 |
| sc MX-1 | 90 | 15–19 | — | >37.2 | 3/5 |
| sc HT29 | 90 | 14–18 | — | 6.0 | 0/5 |
| sc CAKI-1 | 90 | 19–23 | — | 14.5 | 0/5 |
| Penclomedine | | | | | |
| sc MX-1 | 135 | 12–16 | — | >41.0 | 5/5 |
| ic MX-1 | 90 | 1–5 | +88 | — | 0/5 |
| ic MX-1 | 90[d] | 1–5 | +72 | — | 0/5 |
| sc-MX-1 | 135 | 13–17 | — | >38.5 | 5/5 |
| sc MX-1 | 135 | 15–19 | — | >37.2 | 5/5 |

TABLE 2-continued

Antitumor Activity of 4-Demethylpenclomedine and Penclomedine

| Tumor[a] | Optimal IP Dosage (≤LD$_{10}$) (mg/kg/dose) | Schedule (days) | Median % ILS[c] (dying mice only) | T-C[b] (days) | Tumor-Free Survival/Total |
|---|---|---|---|---|---|
| sc HT29 | 135 | 14–18 | — | 1.5 | 0/5 |
| sc CAKI-1 | 135 | 19–23 | — | 15.3 | 0/5 |

[a]Athymic mice (Ncr-nu) were implanted either intracranially (ic) with 18 human MX-1 mammary tumor cells or subcutaneously (sc) with fragments of human tumors (CAKI-, renal; HT29, colon; MX-1, mammary).
[b]The difference in the median of time poststaging for tumors to double in mass: T (treated mice), C (control mice)
[c]% ILS (increased life span) values are not provided where the mice were sacrificed when tumors reached 4 g mass.
[d]Oral treatment (by garage).
[e]Highest dosage level.

EXAMPLE 4

This Example illustrates the methodology employed in the identification and measurement of the distribution of penclomedine and its metabolites in plasma and tissues.

CD2F$_1$ Mice were obtained from Harlan Sprague-Dawley (Frederick, Md.). During the course of this study, mice were housed in polyethylene shoe box cages without bedding and given access to food and water. Four mice were used per time point.

$^{14}$C-Penclomedine (specific activity 17.6 and 18.9 mCi/mM, labeled at CCl$_3$) was obtained from Research Triangle Institute (Research Triangle Park, N.C.) and stored at −20° C. The site of radiolabel has been conserved in all penclomedine metabolites identified to date. The composition of the radioactive material was determined to be 99% $^{14}$C-penclomedine, by HPLC coupled with radiochemical detection.

$^{14}$C-penclomedine (1 mCi/ml in ethanol) was added to the clinical penclomedine emulsion to give an activity of 40 mCi/ml (4% ethanol final concentration). The mice were administered the above penclomedine formulation at 40 mg/kg (120 mg/m$^2$, >>100 ml/animal) either intravenously via tail vein or orally via gavage. At 1, 2, 4, and 22 hours after intravenous administration and 2,4, 6, and 22 hours after oral administration, animals were euthanized with carbon dioxide and blood tissues were collected. Blood tissues from each time point were pooled. Blood was centrifuged and plasma and red cells were separated; tissues were homogenized in 3 volumes of 100 mM ammonium formate buffer pH 6.5. Urinary output was estimated by washing the cages with water after removing food and feces and concentrating these cage washings.

A 1 ml aliquot of tissue homogenate or a 200 ml of plasma was acidified with 200 ml of 0.7 M ammonium phosphate pH 2.7, then 3 ml of ethyl acetate was added. This mixture was vortexed, centrifuged and the organic layer was collected. Fifty microliters of DMSO were added, and the ethyl acetate was concentrated to approximately 100 ml with a stream of dry nitrogen. Fifty microliters of acetonitrile were added to this residue, and the resulting solution was analyzed by HPLC. Human plasma was processed identically to mouse plasma with the exception that 500 ml of plasma was extracted. Concentrated cage washings were analyzed by HPLC without further processing.

Plasma and tissue protein binding data were measured on the residue of the above extractions. The aqueous phase was washed with 5 ml of ethanol, centrifuged, and the ethanol insoluble precipitate was washed again with 5 ml ethanol. After centrifugation the pellet was resuspended in 0.5 ml 6 M guanidinium chloride, added to 10 ml 3a70B scintillation cocktail (Research Products International Corp., Mount Prospect, Ill.), and counted for $^{14}$C.

HPLC Assays: The HPLC system consisted of a Hewlett-Packard Series II 1090 liquid chromatograph with diode array detector (Hewlett-Packard, Palo Alto, Calif.). The column used was an Alltech Adsorbosphere HS C18 5 m 250×4.6 mm column (Alltech Associates, Deerfield, Ill.). The system used a gradient elution consisting of 100% 10 mM ammonium phosphate buffer pH 2.7 progressing to 100% acetonitrile over 25 minutes at 1 ml/min. Detection was performed by means of ultraviolet absorbance at 240 nm as well as by means of radioactivity using a Radiomatic Flo-One/Beta A140 radioactive flow detector (Packard Instrument Co., Downers Grove, Ill.) equipped with a 500 ml liquid cells and Flo-Scint VI scintillation cocktail at a 2:1 ratio.

GC/EI/MS Metabolite Identification: Metabolites were identified by comparing the mass spectra of the incubation extracts with those of synthetic standards. Mass spectra were obtained on a Hewlett Packard 5890 Series II Gas Chromatograph equipped with Model 5971 Mass Selective Detector. Compounds were separated on a 20 m×0.25 mm i.d. DB-5 fused silica capillary column (Alltech Associates, Deerfield, Ill.). Helium was used as the carrier gas at a flow rate of 0.6 ml/min; the temperatures of the injector and transfer lines were 200 and 270° C., respectively. The column temperature was held at 150° C. for 4 minutes after sample injection and then linearly increased to 290° C. at a rate of 10° C./min.

Sample Preparation for GC/EI/MS: Plasma and tissue homogenates were extracted with ethylacetate and organic phase evaporated with a stream of dry nitrogen. Samples were either reconstituted in ethylacetate and injected directly (2 ml) into the GC or reacted with N,O-bis(trimethylsilyl) trifluoroacetamide (BSTFA) (Supelco Inc., Bellefonte, Pa.).

EXAMPLE 5

This Example illustrates an advantage of using demethylpenclomedine as a cancer treatment drug in comparison to penclomedine. Particularly, this Example illustrates that demethylpenclomedine does not accumulate in fatty tissues as much as penclomedine.

$^{14}$C-Penclomedine derived radioactivity was determined in mouse urine samples collected at 1, 2, 4, and 22 hours following intravenous and oral administration of $^{14}$C-penclomedine. Penclomedine and a number of metabolites could be detected in most mouse tissues as set forth in Table 3. All 2 hour tissue samples contained detectable amounts of penclomedine. There were considerable differences in metabolite distribution among the different tissues. For example, liver contained the highest levels of demethylpenclomedine and the lowest levels of penclomedine. Highest levels of penclomedine were detected in the fat and carcass. Most compounds present in the 2 hour samples were detectable in the 22 hour samples at levels from 10% to 50% of those seen at 2 hours.

TABLE 3

Distribution of Penclomedine and its Metabolites in Mouse Tissues

| | | Tissue Concentration (nmoles/gram wet tissue) | | | | | | | |
|---|---|---|---|---|---|---|---|---|---|
| | | Demethyl-Dechloro-Penclomedine[1] | | Demethyl-Penclomedine | | Dechloro-Penclomedine[2] | | Penclomedine | |
| Tissue | Time (hours) | i.v. | p.o | i.v | p.o | i.v | p.o | i.v. | p.o |
| Liver | 2 | 9.15 | 8.5 | 40.5 | 28.8 | n.d.* | n.d. | 0.69 | 1.35 |
| | 22 | 1.73 | 0.63 | 13.5 | 5.65 | n.d. | n.d. | n.d. | 0.38 |
| Kidney | 2 | 4.02 | 6.10 | 13.7 | 13.0 | 0.39 | 0.87 | 6.45 | 7.30 |
| | 22 | 1.44 | 0.75 | 4.89 | 2.08 | n.d. | n.d. | 1.21 | 0.85 |
| Brain | 2 | 1.18 | 1.10 | 2.02 | 3.36 | 0.26 | 0.56 | 1.30 | 2.16 |
| | 22 | 0.32 | n.d. | 0.54 | 0.54 | n.d. | n.d. | n.d. | n.d. |
| Fat | 2 | n.d. | n.d | 3.43 | 4.46 | n.d. | n.d. | 15.8 | 18.55 |
| | 22 | n.d. | — | 0.40 | — | 0.36 | — | 8.90 | — |
| Carcass | 2 | 9.00 | 6.25 | 11.4 | 10.3 | 2.30 | 3.95 | 14.8 | 55.2 |
| | 22 | 2.16 | 1.14 | 2.85 | 0.85 | 0.22 | 1.21 | 5.15 | 2.16 |

*n.d. = not detectable;
[1]3,5-dichloro-2-methoxy-4-hydroxy-6-(dichloromethyl)pyridine;
[2]3,5-dichloro-2,4-dimethoxy-6-(dichloromethyl)pyridine.

Differences in metabolite distribution among different tissue been observed in rats. O'Reilly et al., *Clin. Cancer Res.*, 2, 541–548, March 1996. The differences demonstrate that penclomedine but not its metabolite is detectable in the nervous system during the time period of neurologic symptoms.

EXAMPLE 6

This example illustrates the distribution of penclomedine and 4-demethylpenclomedine in human plasma during a 5 day treatment schedule using penclomedine.

Figure 2:
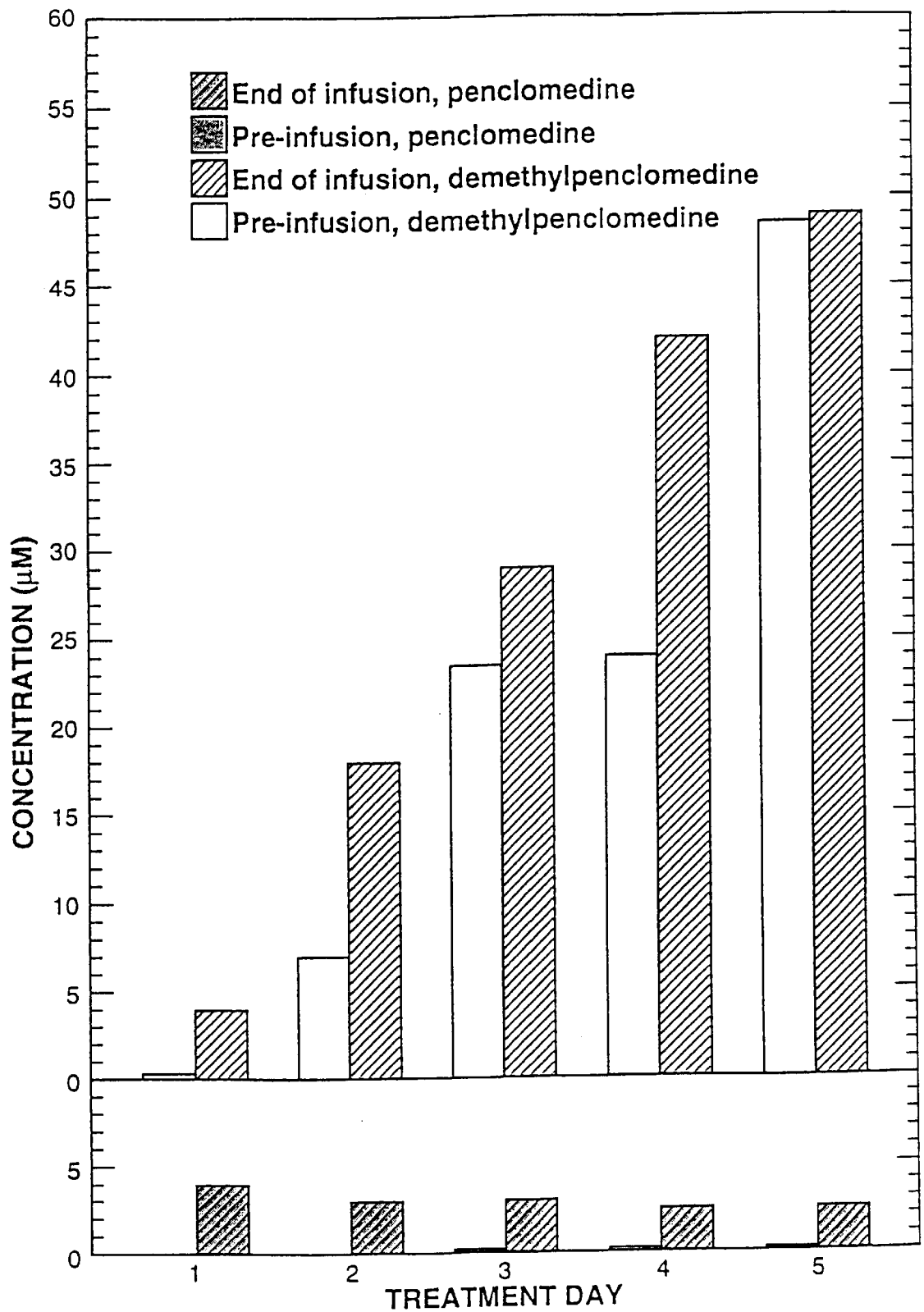
FIG. 2 depicts the penclomedine (gray shade) and demethylpenclomedine (white) levels in human plasma on each of five treatment days. Data are from a single patient and are typical. The same ordinate scale is used for both penclomedine and demethylpenclomedine. Pre-infusion levels are depicted without cross hatchings; end of infusion levels are depicted with cross hatchings.

Plasma levels of the metabolite and penclomedine were determined in 9 patients during the 5 day treatment schedule. After an initial 1 hr i.v. infusion of penclomedine (315 mg/m$^2$), drug levels rapidly declined in an apparently biexponential fashion as shown in FIG. 1 for a single individual. Demethylpenclomedine plasma levels were equal to penclomedine plasma levels by 10 min after end of the infusion and rose to 9.5 $\mu$M by 7 hrs. In five day pre-infusion and post-infusion plasma samples obtained from the same patient penclomedine was barely detectable in pre-infusion samples and were always less than $\mu$M in the post-infusion samples (see FIG. 2). The ratio of demethylpenclomedine to penclomedine in the post-infusion plasma sample obtained on day 1 of treatment was approximately 1:1; however, impressive accumulation of demethylpenclomedine was noted during the five day treatment schedule and by the final day this ratio was often greater than 10. This metabolite persisted in the plasma for an extended period of time, producing at five days plasma exposures of the metabolite nearly 400 times that of the parent drug, as calculated by the area under the concentration-time curve. A summary of post-infusion demethylpenclomedine plasma levels determined on each day of treatment for 9 patients is set forth in Table 4. While there was an insufficient number of patients at each dose level to allow statistical analysis of the means, accumulation of metabolite was observed in all 9 patients over the 5 day treatment.

TABLE 4

Accumulation of demethylpenclomedine in patients during a 5 day treatment schedule with penclomedine

| | | Treatment Day | | | | |
|---|---|---|---|---|---|---|
| Patient Number | Dose (mg/m$^2$) | 1 | 2 | 3 | 4 | 5 |
| 1 | 90 | 1.1 | 5.1 | 4.0 | 8.2 | — |
| 2 | 135 | 1.6 | 5.1 | 6.1 | 11.5 | 22.4 |
| 3 | 135 | 0.6 | 4.8 | 7.0 | 5.7 | 19.0 |
| 4 | 180 | 8.2 | — | 17.9 | 38.1 | 51.7 |
| 5 | 180 | 2.7 | 7.7 | 16.1 | 26.7 | 42.6 |
| 6 | 236 | 1.2 | 7.9 | 19.1 | 28.7 | 35.4 |
| 7 | 236 | 0.9 | 6.7 | 17.6 | 31.3 | 32.2 |
| 8 | 315 | 1.5 | 5.9 | 14.2 | 15.6 | 25.6 |
| 9 | 315 | 3.8 | 17.9 | 29.1 | 41.3 | 50.0 |

All of the references cited herein including the patent and publications are hereby incorporated in their entireties by reference.

While this invention has been described with an emphasis upon the preferred embodiment, it will be obvious to those of ordinary skill in the art that variations of the preferred embodiment may be used and that it is intended that the invention may be practiced otherwise than as specifically described herein. Accordingly, this invention includes all modifications encompassed within the spirit and scope of the invention as defined by the following claims.

What is claimed is:

1. Substantially pure 3,5-dichloro-2-methoxy-4-hydroxy-6-(trichloromethyl)pyridine or a pharmaceutically acceptable acid addition salt thereof.

2. A pharmaceutical composition comprising 3,5-dichloro-2-methoxy-4-hydroxy-6-(trichloromethyl)pyridine or a pharmaceutically acceptable acid addition salt thereof and a pharmaceutically acceptable carrier.

3. A method of treating cancer in a mammal comprising administering to said mammal a cancer treatment amount of 3,5-dichloro-2-methoxy-4-hydroxy-6-(trichloromethyl)pyridine or a pharmaceutically acceptable acid addition salt thereof.

4. The method of claim 3, wherein said cancer is selected from the group consisting of a mammary tumor, a brain tumor, a colon tumor, a renal tumor, an ovarian tumor, neuroblastoma, and retinoblastoma.

5. The method of claim 4, wherein said cancer is selected from the group consisting of a mammary tumor, a colon tumor, and a renal tumor.

6. The method of claim 3, wherein said treatment amount is from about 5 mg/kg to about 200 mg/kg of the body weight of said mammal.

7. The method of claim 6, wherein said treatment amount is from about 5 mg/kg to about 100 mg/kg of the body weight of said mammal.

8. The method of claim 3, wherein said treatment is carried out over a period of from one day to about 24 months.

9. The method of claim 3, wherein said 3,5-dichloro-2-methoxy-4-hydroxy-6-(trichloromethyl)pyridine or pharmaceutically acceptable acid addition salt thereof is administered orally or intravenously.

10. The method of claim 3, wherein said mammal is human.

11. The method of claim 5, wherein said treatment amount is from about 5 mg/kg to about 200 mg/kg of the body weight of said mammal.

12. The method of claim 5, wherein said treatment is carried out over a period of from one day to about 24 months.

13. The method of claim 6, wherein said treatment is carried out over a period of from one day to about 24 months.

14. The method of claim 7, wherein said treatment is carried out over a period of from one day to about 24 months.

15. The method of claim 5, wherein said 3,5-dichloro-2-methoxy-4-hydroxy-6-(trichloromethyl)pyridine or pharmaceutically acceptable acid addition salt thereof is administered orally or intravenously.

16. The method of claim 6, wherein said 3,5-dichloro-2-methoxy-4-hydroxy-6-(trichloromethyl)pyridine or pharmaceutically acceptable acid addition salt thereof is administered orally or intravenously.

17. The method of claim 7, wherein said 3,5-dichloro-2-methoxy-4-hydroxy-6-(trichloromethyl)pyridine or pharmaceutically acceptable acid addition salt thereof is administered orally or intravenously.

* * * * *